US006049159A

United States Patent [19]

Barthe et al.

[11] Patent Number: 6,049,159

[45] Date of Patent: Apr. 11, 2000

[54] WIDEBAND ACOUSTIC TRANSDUCER

[75] Inventors: Peter G. Barthe, Phoenix; Michael H. Slayton, Tempe, both of Ariz.

[73] Assignee: Albatros Technologies, Inc., Mesa, Ariz.

[21] Appl. No.: 08/944,261

[22] Filed: Oct. 6, 1997

[51] Int. Cl.[7] .............................. A61B 8/00; H01L 41/08

[52] U.S. Cl. .............................. 310/334; 310/326

[58] Field of Search .............................. 310/322, 326, 310/334, 327, 335; 181/139, 142

[56] References Cited

U.S. PATENT DOCUMENTS

| | | | |
|---|---|---|---|
| 2,427,348 | 9/1947 | Bond et al. | 310/327 |
| 4,166,967 | 9/1979 | Benes et al. | 310/322 |
| 4,211,948 | 7/1980 | Smith et al. | 310/322 |
| 4,211,949 | 7/1980 | Brisken et al. | 310/322 |
| 4,507,582 | 3/1985 | Glenn | 310/327 |
| 4,672,591 | 6/1987 | Breimesser et al. | 367/152 |
| 4,680,499 | 7/1987 | Umemura et al. | 310/334 |
| 4,771,205 | 9/1988 | Mequio | 310/334 |
| 5,030,874 | 7/1991 | Saito et al. | 310/334 |
| 5,070,879 | 12/1991 | Herres | 128/660.08 |
| 5,163,436 | 11/1992 | Saitoh et al. | 310/335 |
| 5,212,671 | 5/1993 | Fujii et al. | 367/151 |
| 5,305,756 | 4/1994 | Entrekin et al. | 128/660.09 |
| 5,327,895 | 7/1994 | Hashimoto et al. | 128/662.03 |
| 5,392,259 | 2/1995 | Bolorforosh | 310/334 |
| 5,396,143 | 3/1995 | Seyed-Bolorforosh et al. | 310/334 |
| 5,423,220 | 6/1995 | Finsterwald et al. | 73/642 |
| 5,438,998 | 8/1995 | Hanafy | 310/334 |
| 5,503,152 | 4/1996 | Oakley et al. | 128/661.01 |
| 5,526,815 | 6/1996 | Granz et al. | 128/660.03 |
| 5,558,092 | 9/1996 | Unger et al. | 128/660.03 |
| 5,644,085 | 7/1997 | Lorraine et al. | 310/334 |
| 5,706,252 | 1/1998 | Le Verrier et al. | 310/334 |
| 5,706,564 | 1/1998 | Rhyne | 310/327 |
| 5,779,644 | 7/1998 | Eberle et al. | 600/463 |
| 5,792,058 | 8/1998 | Lee | 600/459 |
| 5,810,009 | 9/1998 | Mine et al. | 310/334 |

FOREIGN PATENT DOCUMENTS

| | | | |
|---|---|---|---|
| 190 948 | 8/1986 | European Pat. Off. | 310/327 |
| 0 490 260 A2 | 6/1992 | European Pat. Off. | B06B 1/06 |
| 60-12899 | 1/1985 | Japan | 310/327 |

*Primary Examiner*—Thomas M. Dougherty
*Attorney, Agent, or Firm*—Snell & Wilmer

[57] ABSTRACT

A transducer according to various aspects of the present invention provides high fractional bandwidth with relatively low degradation of the pulse duration and sensitivity. The transducer includes a back matching layer behind the transducer material. The back matching layer is characterized by an impedance selected to transmit a selected portion of the backwards propagating acoustic energy to an absorption layer. The remaining acoustic energy is reflected in the desired direction of propagation. As a result, the transducer provides enhanced bandwidth without excessive loss of sensitivity or increase in pulse duration.

31 Claims, 9 Drawing Sheets

WIDEBAND ACOUSTIC TRANSDUCER

BACKGROUND OF THE INVENTION

1. Field of the Invention

The invention relates to acoustic transducers, and more particularly, to ultrasonic acoustic transducers having high bandwidth and sensitivity.

2. Description of the Related Art

Since the latter portion of the twentieth century, ultrasonics has developed into an important field for a wide array of applications, such as detecting flaws in engineering, imaging in medicine, and signaling in marine environments. In particular, ultrasound is widely used in the detection of objects in a medium, such as finding the floor of the ocean or underground pipes. Similarly, ultrasound may be used to identify flaws and cracks in a structure.

One of the most well known applications is medical imaging for fetal evaluation, disease detection and identification, and evaluation of internal organs and structures. Ultrasound may also be used to explore characteristics of tumors and cysts that are not disclosed by conventional imaging techniques, such as conventional X-rays. Ultrasonics further facilitates the study of heart motion and the destruction of unwanted cells. The array of ultrasound uses further extends to removing debris from objects, molding plastics, and even acoustic holography.

Many of these developments are possible due to advances in the manufacture of transducers for generating ultrasonic energy. Currently, the available frequencies extend to even the gigahertz range. Crystals of certain materials, such as quartz or other piezoelectric materials, form the foundation of most modern transducers. When an alternating electrical voltage is applied across opposite faces of such a material, the material physically oscillates at the frequency of the alternating voltage. This effect has been identified in a variety of materials.

Frequency, however, is not the only relevant characteristic. For example, medical imaging typically requires highly sensitive transducers with wide bandwidth. In addition, minimal pulse duration is desirable for optimal resolution. These objectives, however, typically conflict. Measures taken to increase the bandwidth of the transducer tend to decrease the pulse duration but diminish the sensitivity. Similarly, adjusting the configuration of a transducer to improve the sensitivity tends to diminish the bandwidth of the transducer.

As an illustrative example, the performance characteristics of a conventional transducer are shown in FIGS. 8A–D. After the transducer is well-matched to its frontal matching layers, bandwidth may only be increased by increasing the backing impedance. As the backing impedance (ZB) increases from 1.5 MRayl to 10 MRayl, the sensitivity of the transducer (Vpp) diminishes from about 1.8 V peak-to-peak to 0.85 V peak-to-peak, a loss of about 6.5 dB. In addition, the increased impedance of the backing may undesirably increase the pulse duration, as may be observed in FIG. 8B for backing impedances greater than about 6.5 MRayl. Thus, the configuration of the transducer tends to represent a compromise between competing considerations of sensitivity, bandwidth, and pulse duration.

SUMMARY OF THE INVENTION

A transducer according to various aspects of the present invention provides high fractional bandwidth with relatively low degradation of the pulse duration and sensitivity. The transducer includes a back matching layer and a back absorption layer behind the transducer material. The back matching layer is characterized by an impedance selected to transmit a selected portion of the backwards propagating acoustic energy to an absorption layer. The remaining acoustic energy is reflected in the desired direction of propagation. As a result, the transducer provides enhanced bandwidth without excessive loss of sensitivity or increase in pulse duration.

In particular, a transducer according to various aspects of the present invention includes a transducer material, suitably separated into individual elements, and at least one frontal matching layer. In addition, the transducer includes a back matching layer disposed between the transducer material and a back absorption layer. The back matching layer is configured to transmit a selected portion of the incident acoustic energy to the back absorption layer and reflect a portion towards the front of the transducer.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing, in which like parts may be referred to by like numerals:

DETAILED DESCRIPTION OF PREFERRED EXEMPLARY EMBODIMENTS

Figure 1:
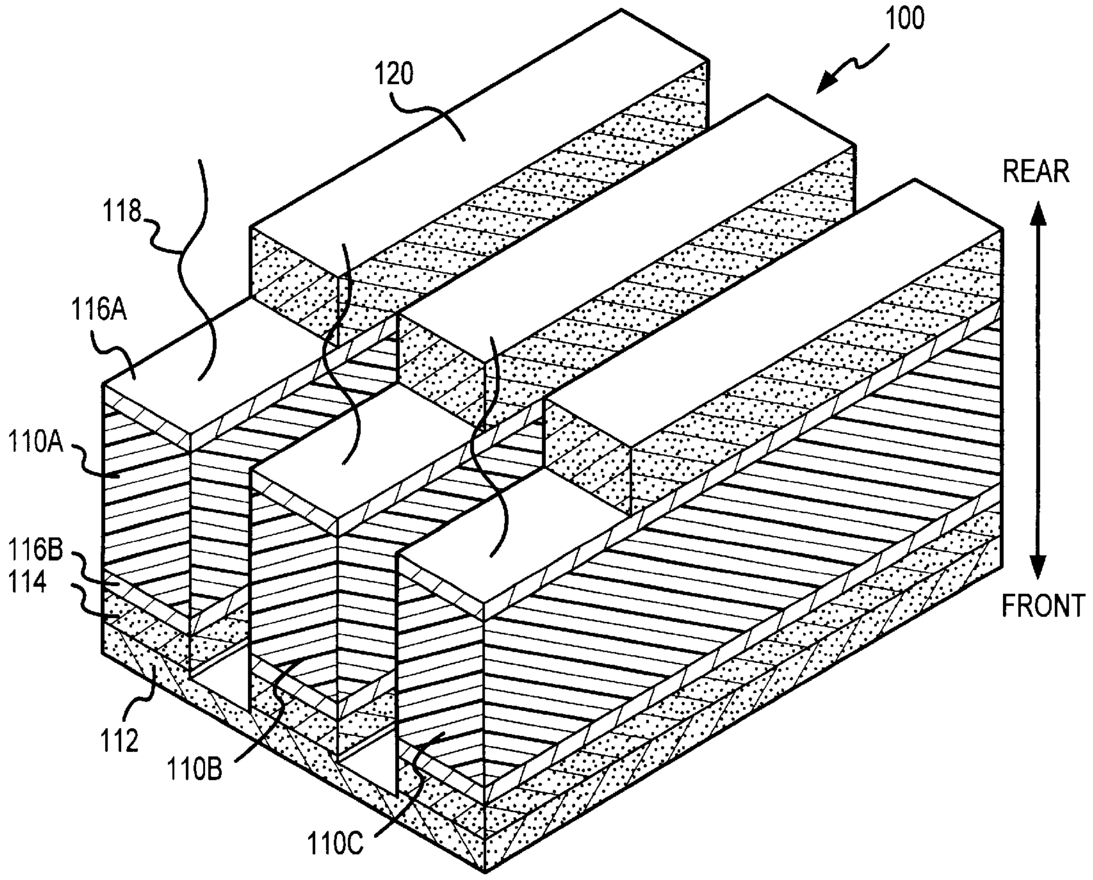
FIG. 1 is a cutaway view of a transducer according to various aspects of the present invention.
Figure 2:
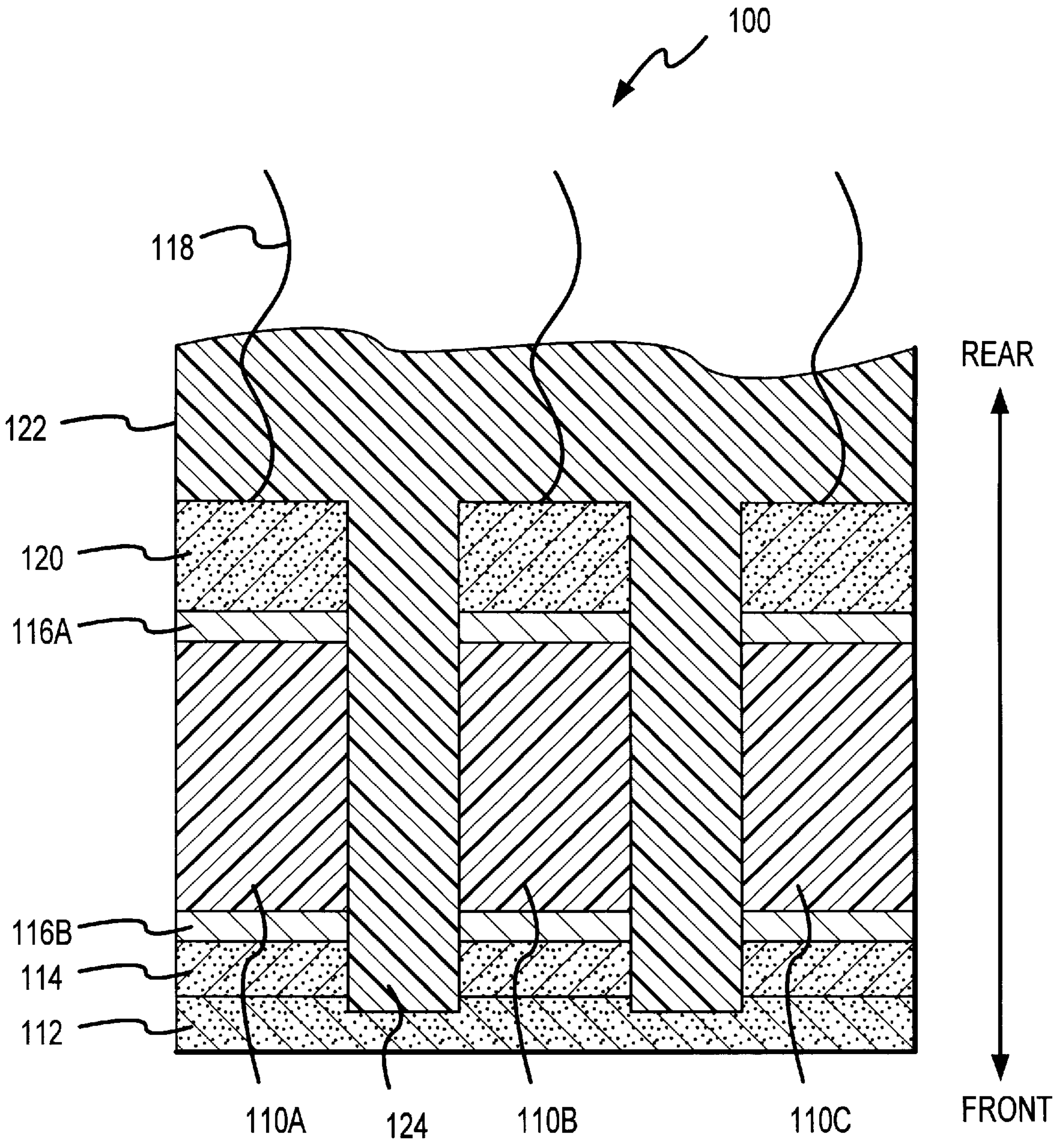
FIG. 2 is cross section view of the transducer of FIG. 1.

Referring now to FIGS. 1 and 2, an acoustic transducer 100 according to various aspects of the present invention comprises a transduction material 110; at least one frontal matching layer 112; a pair of electrical connection layers 116A–B; at least one electrical bus 118; a back matching layer 120; and a back absorption layer 122. Additional components, such as additional frontal matching layers, a physical interface, and the like, may be further included as described in greater detail below.

The transduction material 110 transforms one form of energy to another. For example, the transduction material 110 suitably transforms electrical energy into acoustic energy and vice versa. In the present embodiment, the transduction material 110 comprises any suitable piezoelectric material, such as piezoelectric ceramics, piezoelectric crystals, piezoelectric plastics, or piezoelectric composite materials, including lithium niobate, lead zirconate titanate, lead titanate, barium titanate, or lead metaniobate. Preferably, the transduction material 110 is comprised of a rigid, high strength material to facilitate dicing, as discussed in greater detail below.

The transduction material 110 is suitably separated or partially separated to define a plurality of transduction elements 110A–C. Preferably, each of the transduction elements 110A–C is substantially acoustically isolated from the other transduction elements 110A–C. A single piezoelectric piece may be separated into individual transduction elements 1 10 in any suitable manner and configuration. In the present embodiment, the transduction elements 110 are formed by dicing the transduction material 110 using a conventional industrial dicing saw to form a 2—2 composite of piezoelectric material. The size of the transducer elements may be varied according to the desired characteristics of the transducer, such as the desired acoustic wavelength and the speed of sound in the transduction material 110. The channels between the transduction elements 110A–C in the present embodiment are suitably 0.8 mil to 2 mil wide and one-half to one and a half acoustic wavelengths apart. The resulting array of transduction elements 110 may comprise any number of elements, such as 128 elements in a one dimensional array, 640 elements in a 128 by 5 array, 4096 elements in a 64 by 64 array, 12 elements in an annular array, or one element in a single element transducer.

In addition, a transducer 100 according to various aspects of the present invention suitably includes an interelement filler 124. The interelement filler 124 is disposed in the channels between the transduction elements 110 to isolate the transduction elements 110 from one another. Preferably, the interelement filler 124 is comprised of an acoustically lossy material to absorb laterally propagating acoustic energy, thus tending to reduce lateral resonance and isolate the various transduction elements 110.

The electrical connection layers 116 are disposed adjacent to and in electrical contact with the transduction material 110, for example on the front and rear surfaces of each transduction element 110, to facilitate the application of an electric potential across each transduction element 110. The electrical connection layers 116 may be comprised of any suitable conductive material, such as gold, silver, nickel, chrome, or a palladium/silver alloy. In addition, each electrical connection layer 116 may comprise a single sheet or a laminate formed of conductive materials. Each electrical connection layer 116 may be further separated in a manner like that of the transduction material 110 so that each transduction element 110 is connected to a portion of each electrical connection layer 116. The various portions of each electrical connection layer 116 are electrically connected so that electric signals may be applied to all of the transduction elements 110 simultaneously. The electrical connection layers 116 may be connected to the terminals of a conventional driver or receiver circuit via buses 118 to drive the transducer 100 with electric signals or receive the electric signals generated by the transduction material 110.

The frontal matching layer 112 is suitably adjacent to the front electrical connection layer 116B in the desired direction of propagation, i.e., in front of the front electrical connection layer 116B. Preferably, a transducer 100 according to various aspects of the present invention includes at least two frontal matching layers 112, 114, though the transducer 100 may be configured with any number of frontal matching layers. Each layer 112, 114 is conventionally configured to transmit acoustic energy to or from the transduction elements 110A–C. To create an interface with minimal impedance differential between the transduction material 110 and the frontal matching layers 112, 114, each frontal matching layer 112, 114 is suitably one-quarter of a wavelength thick based on the desired center frequency and the speed of sound propagation in the material. In addition, each layer 112, 114 is comprised of a material having characteristics tending to minimize the impedance mismatch at the boundaries between the transduction material 110 and the rear frontal matching layer 114, the rear frontal matching layer 114 and the forward frontal matching layer 112, and the forward frontal matching layer 112 and the body to which the transducer 100 is applied or a physical interface (not shown) as described below. The frontal matching layers 112, 114 are comprised of any suitable material, like a polymer, for example an epoxy, powder-filled epoxy, porcelain, silicon or silicon glass, quartz glass, polyvinyl chloride, or polyvinylidene fluoride. In addition, the rear frontal matching layer 114 may be combined with the front electrical connection layer 116B by forming the rear frontal matching layer 114 from a conductive material having appropriate acoustic properties. Although not shown, in a 1-D, a 1.5-D array, or a 2-D array, the transducer 100 may be curved or focused in the elevation direction to form an image slice. Likewise, in single-element or annular arrays a spherical focus is used. Alternatively, flat transducers may be used with acoustic lenses attached to the front layers.

The frontal matching layers 112, 114 are suitably covered with a physical interface (not shown). Preferably, the physical interface comprises an substantially acoustically transparent material, such as rubber or other filler, between the frontal matching layers 112, 114 and a body against which the transducer 100 is to be placed. Alternatively, the physical interface suitably comprises an acoustic lens to adjust the propagation direction of the acoustic waves.

The back matching layer 120 is suitably disposed adjacent the rear electrical connection layer 116A on the opposite side of the transduction material 110. Like the frontal matching layer 112, the back matching layer 120 may be comprised of any suitable material, like a polymer, for example an epoxy, powder-filled epoxy, porcelain, silicon or silicon glass, quartz glass, polyvinyl chloride, or polyvinylidene fluoride. Preferably, the back matching layer 120 is configured to facilitate optimal bandwidth and sensitivity of the transducer 100. In particular, the back matching layer 120 is configured to transmit a portion of the acoustic energy through the back matching layer 120 and conversely to reflect a portion. The back matching layer 120 is configured to increase the fractional bandwidth of the transducer 100 without losing sensitivity or creating long pulse lengths. Like the frontal matching layers 112, 114, the back matching layer 120 is preferably a quarter-wavelength thick. Further, the back matching layer 120 has an impedance which may be selected according to the particular application or environment in which the transducer 100 is used. For optimal resolution, the pulse duration may be reduced by increasing the impedance of the back matching layer 120. For greater bandwidth, the back matching layer's 120 impedance is suitably reduced. This approach can be used for back matching layer acoustic impedances of any value, including impedances exceeding 10 MRayl. Generally, however, the range of impedances for the back matching layer 120 includes 1.5 MRayl to 10 MRayl, and more preferably, 5 MRayl to 9 MRayl.

The back absorption layer 122 is suitably configured to absorb energy that is transmitted by the back matching layer 120 to prevent the energy from being reflected back towards the front of the transducer 100. In the present embodiment, the back absorption layer 122 is suitably disposed adjacent the rear surface of the back matching layer 120. The back absorption layer 122 may be comprised of any suitable acoustic absorber. In one embodiment, the back absorption layer 122 is comprised of the same material as the interelement filler 124.

Figure 3:
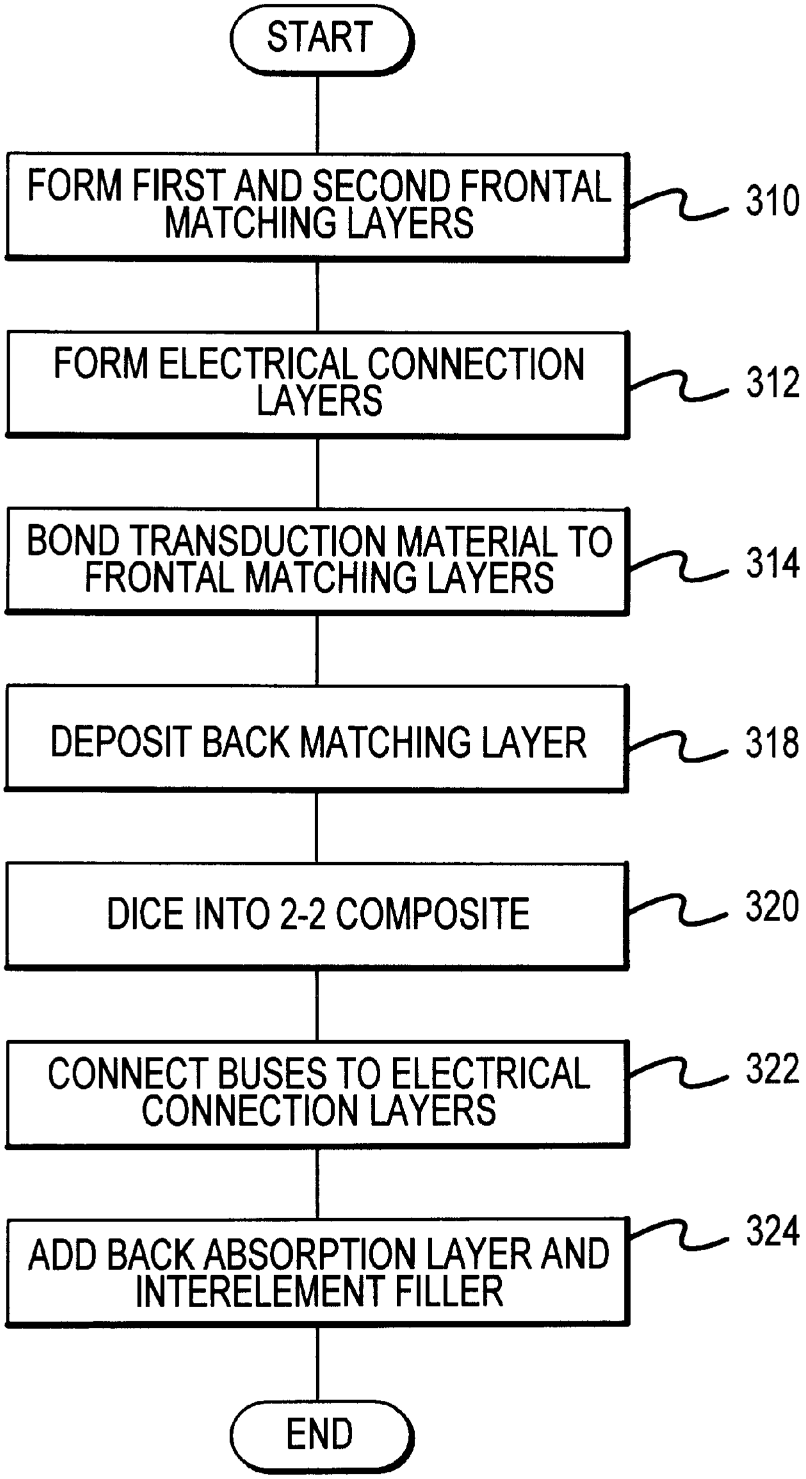
FIG. 3 is a flow chart of a method of manufacturing the transducer of FIGS. 1 and 2.
Figure 4A:
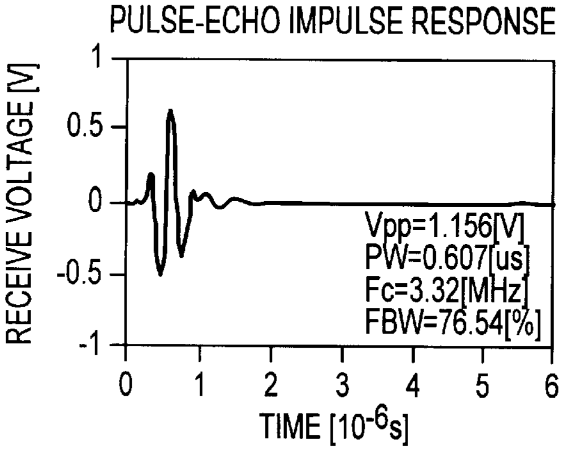
FIGS. 4A–D illustrate the performance characteristics of a conventional transducer.
Figure 4B:
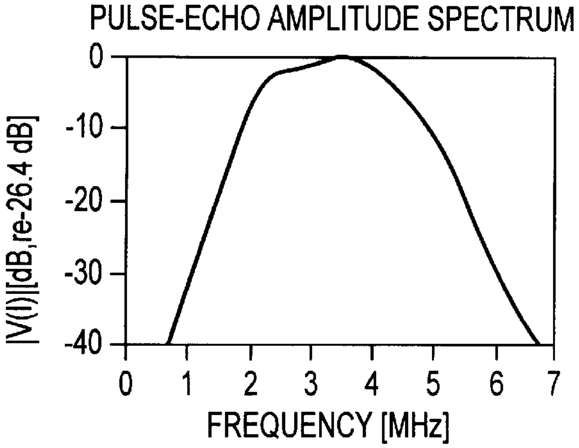
Figure 4C:
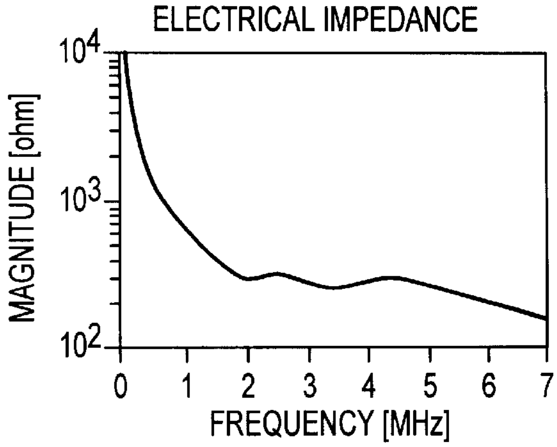
Figure 4D:
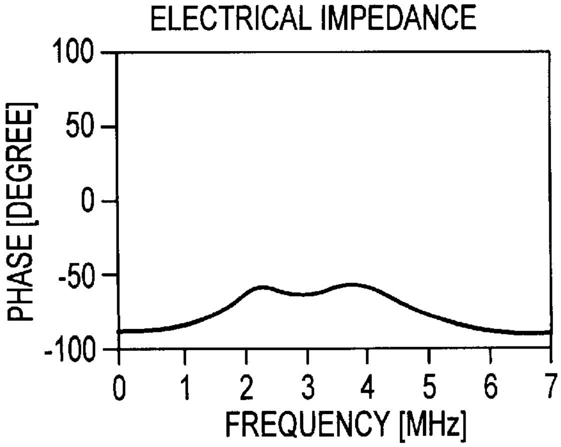
Figure 5A:
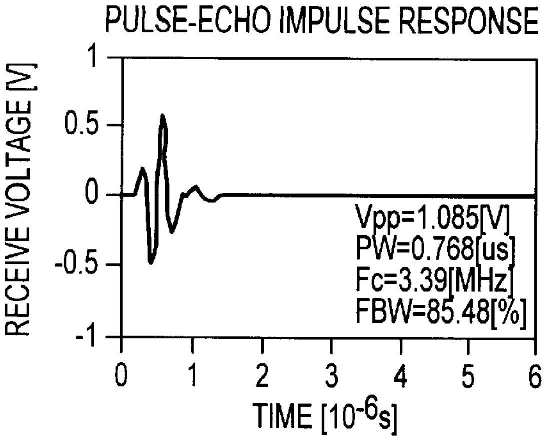
FIGS. 5A–D illustrate the performance characteristics of a transducer according to various aspects of the present invention.
Figure 5B:
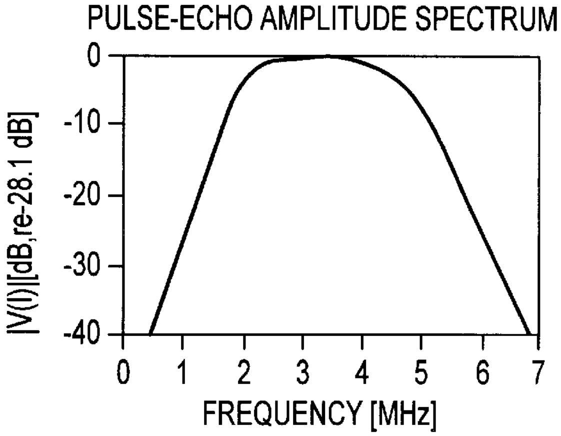
Figure 5C:
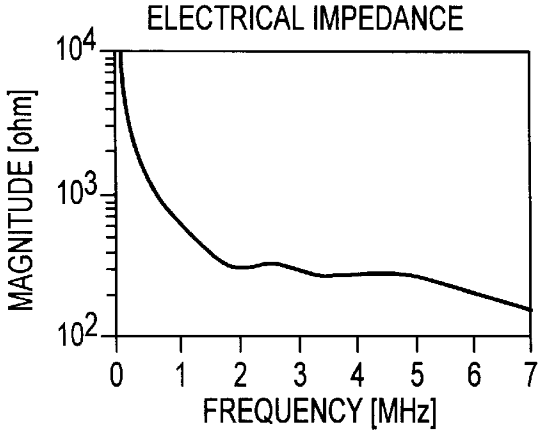
Figure 5D:
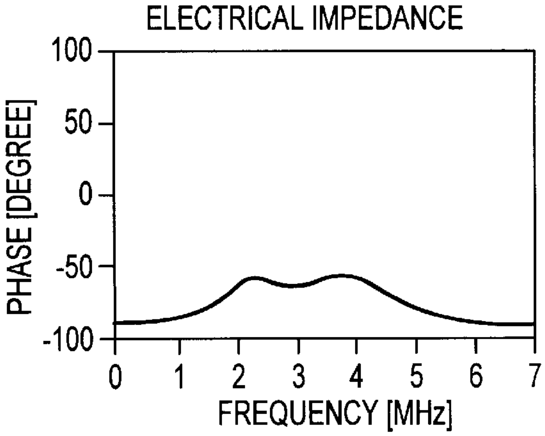

A transducer 100 according to various aspects of the present invention may be created and assembled in any suitable manner. In the present embodiment, referring now to FIG. 3, the frontal matching layers 112, 114 are initially formed (step 310). For example, the forward frontal matching layer 112 is suitably cast, then cut and ground to the desired dimensions. The rear frontal matching layer 114 is, in a similar manner, suitably cast on top of the forward frontal matching layer 112, then cut and ground to the appropriate dimensions. If necessary, each frontal matching layer 112, 114 is allowed to cure.

The electrical connection layers 116A–B are suitably disposed between the front and back surfaces of the transduction material and the rear frontal matching layer 114 and the back matching layer 120, respectively (step 312). The electrical connection layers 116A–B may be deposited, such as on the transduction material 110 itself, in any suitable manner, for example by electroplating, sputtering, vacuum deposition, and the like. The plated transduction material is suitably then bonded to the frontal matching layers (step 314), for example with conductive epoxy or other suitable electrically conductive materials, such that all of the individual front electrical connection layers 116B are bussed to one electrical common ground connection.

Following formation of the electrical connections 116A–B, the back matching layer 120 is formed on the rear surface of the rear electrical connection layer 116A (step 318). A portion of the rear electrical connection layer 116A, however, is suitably not covered with the back matching layer 120 and is left exposed to facilitate the connection of buses 118.

When the assembly comprising the frontal matching layers 112, 114, the electrical connection layers 116, the transduction material 110, and the back matching layer 120 are formed, the assembly is suitably diced to form the individual transduction elements 110 (step 320). In the present embodiment, the channels formed by the dicing process extend through the rear frontal matching layer 114 and partially into the forward frontal matching layer 112. Thus, the forward frontal matching layer 112 supplies structural integrity to the transducer 100 and maintains the relative positions of the various transduction elements 110. In addition, the relatively deep channels, coupled with a resilient front matching layer 112, facilitate the curvature of the transducer 100, for example to form a curved array. The depth of the channels, however, may be varied in any suitable manner. For example, to provide a more rigid transducer assembly, the channels are suitably no deeper than the rear surface of the front electrical connection layer 116B.

Following dicing of the partial transducer assembly, the buses 118 are suitably connected to the respective electrical connection layers 116 (step 322). The interelement filler 124 is then suitably added to the transducer array (step 324). Preferably, the interelement filler 124 initially constitutes a fluid which is suitably poured into the channels formed between the transduction elements 110. When the filler cures, the back absorption layer 122 is suitably added. Alternatively, the back absorption layer 122 may suitably comprise the same material as the interelement filler 124, such that the back absorption layer 122 is provided at the same time as the interelement filler 124.

The back matching layer 120 facilitates a tunable, frequency-dependent acoustic load at the rear face of the transduction material 110. For example, referring now to FIGS. 9A–D, a transducer with a quarter-wavelength back matching layer having an impedance of 6.85 MRayl, exhibits an increase in sensitivity as the backing impedance (ZB) is increased from about 1.8 MRayl to 10 MRayl. The optimal pulse-echo response is where the pulse duration is short, characteristic of a waveform without ringing. In the embodiment of FIGS. 9A–D, the backing impedance should be set to about 6.5 MRayl for best results, yielding a −20 dB pulse duration of 500 nanoseconds.

In another embodiment, the back matching layer 120 of the transducer 100 has an impedance of 6.85 MRayl and a backing material impedance of 6.50 MRayl. As illustrated in FIGS. 5A–D, the transducer, based on computer simulation results, provides a peak-to-peak echo voltage of 1.085 volts and a pulse duration of 0.768 microseconds, comparable to the voltage (sensitivity) and pulse duration of a conventional transducer without a back matching layer as shown in FIGS. 4A–D, which has a backing material impedance of 6.20 MRayl and is otherwise the same as the transducer shown in FIGS. 5A–D. The fractional bandwidth of the transducer with the back layer, however, is 85.48%, compared to a fractional bandwidth of 76.54% for the conventional transducer. In addition, in applications where pulse duration is a more important factor than bandwidth, the impedance of the back matching layer 120 may be increased to reduce the pulse duration.

Figure 6A:
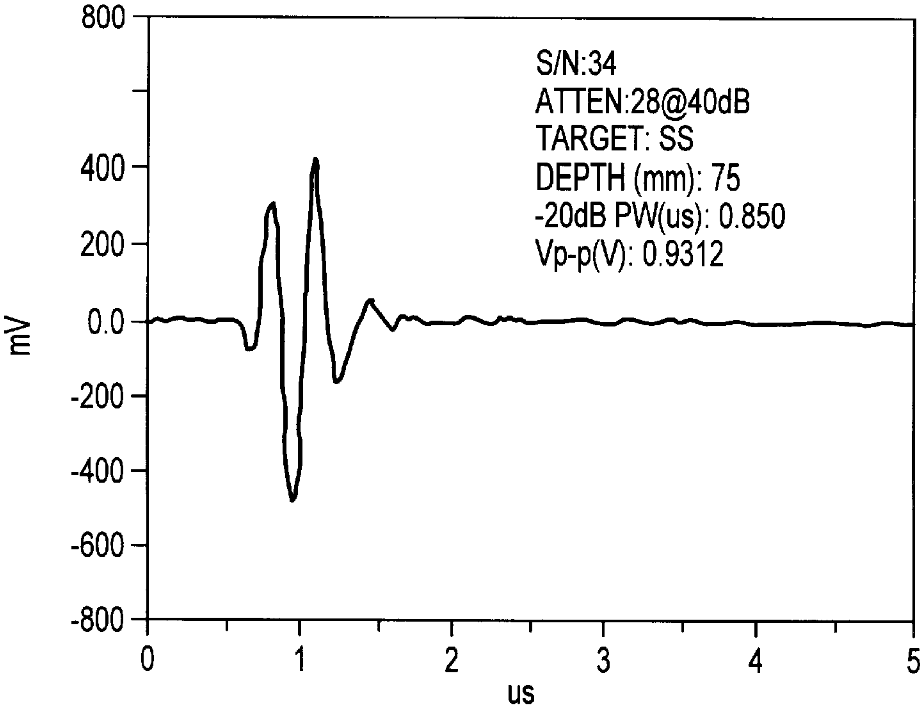
FIGS. 6A–B illustrate the performance characteristics of a second conventional transducer.
Figure 6B:
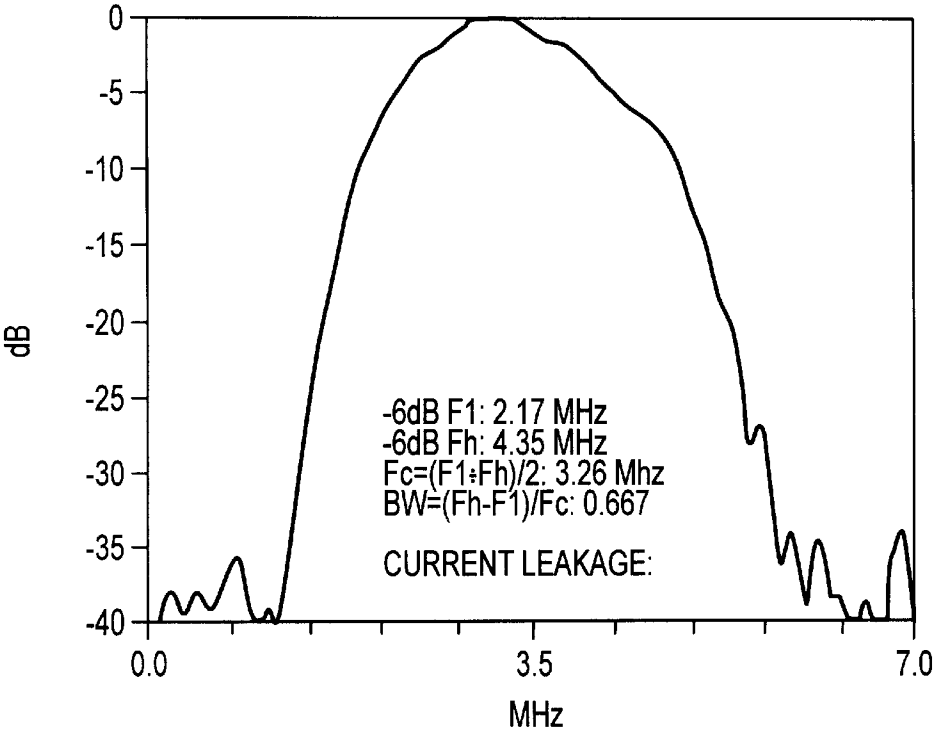
Figure 7A:
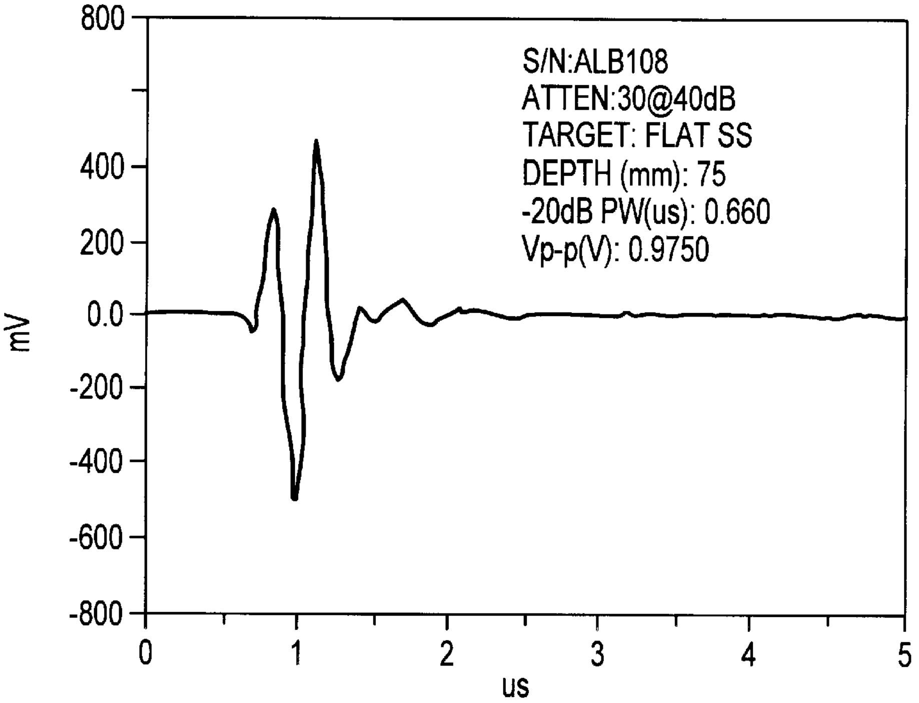
FIGS. 7A–B illustrate the performance characteristics of the second conventional transducer when equipped with a back matching layer and back absorption layer.
Figure 7B:
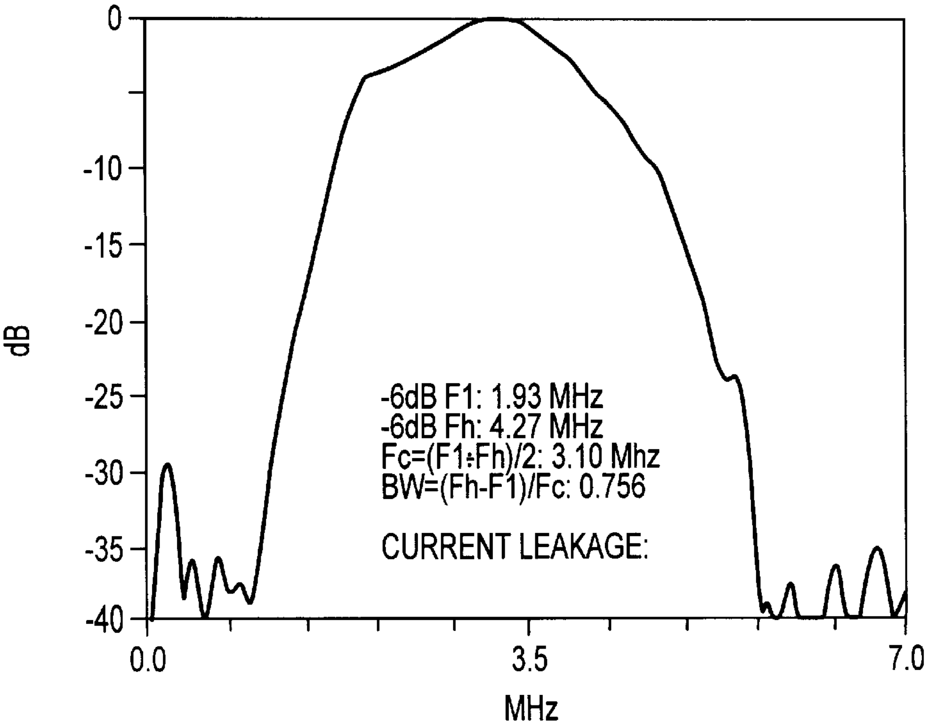
Figure 8A:
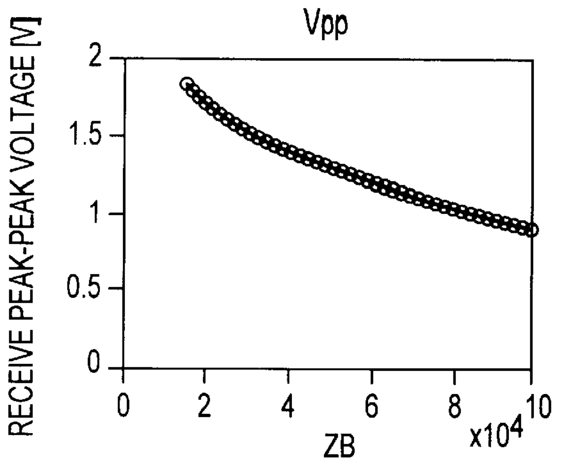
FIGS. 8A–D illustrate the performance characteristics of a conventional transducer.
Figure 8B:
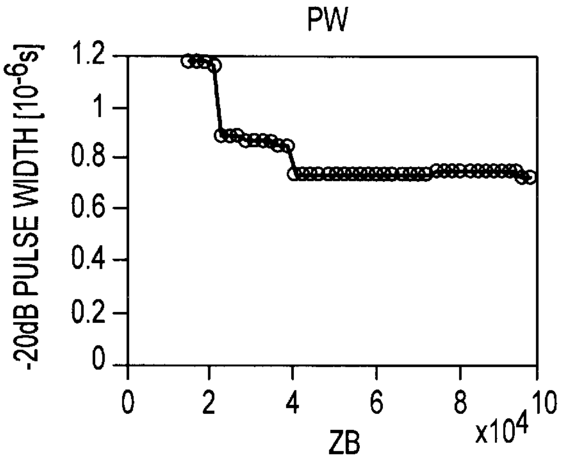
Figure 8C:
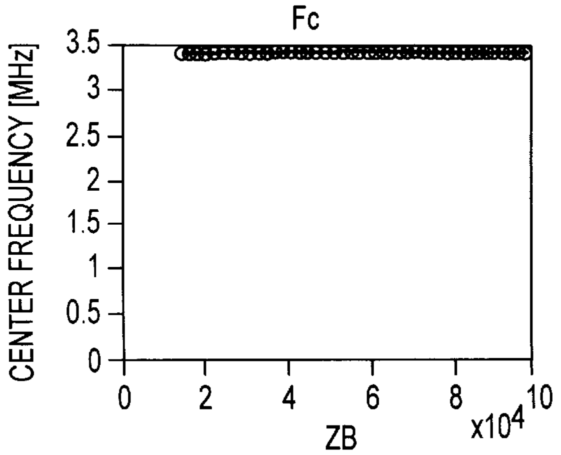
Figure 8D:
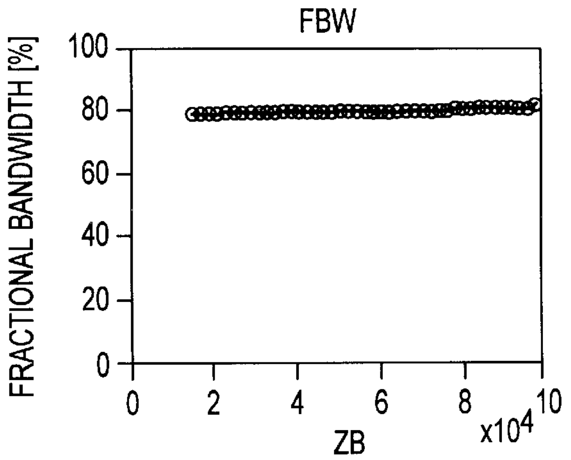
Figure 9A:
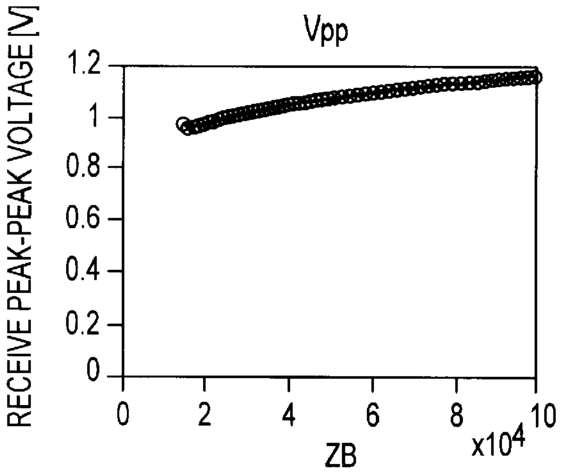
FIGS. 9A–D illustrate the performance characteristics of a transducer according to various aspects of the present invention.
Figure 9B:
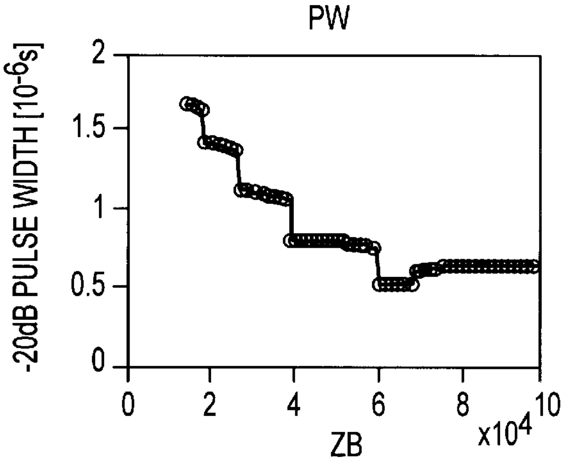
Figure 9C:
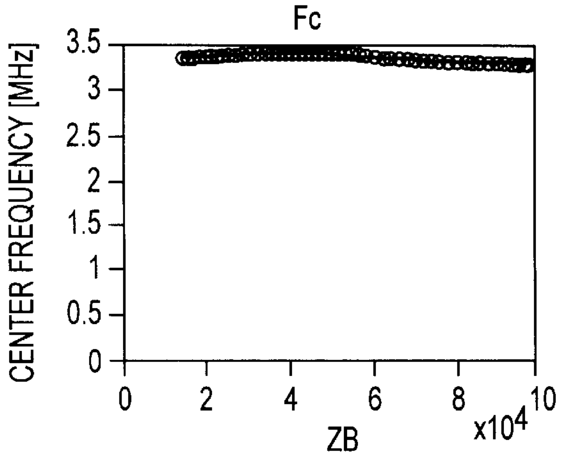
Figure 9D:
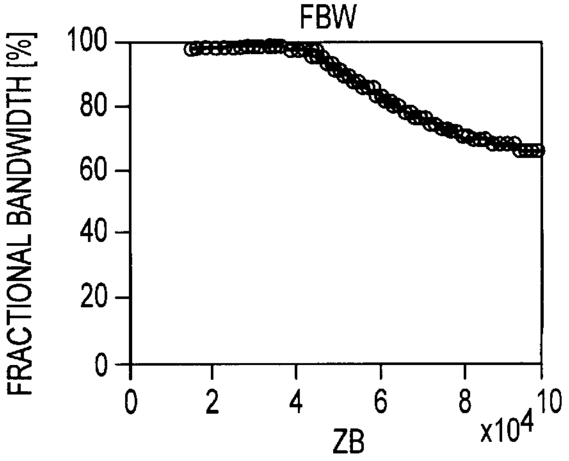

Similarly, experimental measurements on an actual transducer prototype without a back matching layer 120 (FIGS. 6A–B) provides a peak-to-peak echo voltage of 0.931, a −20 dB pulse duration of 0.850 microseconds, and a fractional bandwidth of 66.7% at a center frequency of 3.26 MHz. Referring now to the measured results of FIGS. 7A–B, when a transducer of the same design is equipped with a back matching layer 120 having an impedance of 7 MRayl, the peak-to-peak echo voltage rises to 0.975 volt with 2 dB more attenuation than without the back matching layer for an effective echo voltage of 1.23 volts. Further, the pulse duration drops to 0.660 microseconds and the fractional bandwidth rises to 75.6% at a center frequency of 3.10 MHz.

In sum, a transducer according to various aspects of the present invention includes a back matching layer to provide a variable and frequency-dependent acoustic load, unlike the substantially static load provided by a conventional transducer backing. The presence of the back matching layer provides a back-face reflection coefficient which varies its magnitude and phase versus the frequency. Consequently, the back-face reflection coefficient may be varied to optimize the characteristics of the transducer.

Thus, a transducer according to various aspects of the present invention provides enhanced performance characteristics for various applications. The reduced pulse duration tends to facilitate image resolution. Further, the improved fractional bandwidth may be obtained without sacrificing sensitivity. While the principles of the invention have been described in illustrative embodiments, there will be immediately obvious to those skilled in the art many modifications of structure, arrangements, proportions, the elements, materials and components, used in the practice of the invention which are particularly adapted for a specific environment and operating requirements without departing from those principles.

What is claimed is:

1. An acoustic transducer for propagating sound waves in a desired direction, comprising:

a transduction material;

a backing material disposed behind said transduction material with respect to the desired direction; and a back matching layer disposed between the transduction material and the backing material, wherein said back matching layer is configured to transmit a preselected fraction of a sound wave's energy to said backing material and reflect a preselected fraction of said sound wave's energy towards said transduction material, such that said back matching layer does not completely transmit said sound wave's energy and does not completely reflect said sound wave's energy.

2. An acoustic transducer according to claim 1, wherein said transduction material is comprised of at least one of piezoelectric ceramic, piezoelectric crystal, piezoelectric plastic, piezoelectric composite material, lithium niobate, lead zirconate titanate, lead titanate, barium titanate, and lead metaniobate.

3. An acoustic transducer according to claim 1, wherein said transduction material comprises a plurality of transduction elements, wherein said transduction elements are substantially acoustically isolated from each other.

4. An acoustic transducer according to claim 3, wherein said plurality of transduction elements comprises a 2—2 composite array of transduction elements.

5. An acoustic transducer according to claim 3, wherein said transduction elements are separated by an interelement filler comprised of acoustically lossy material.

6. An acoustic transducer according to claim 1, further comprising an electrical connection layer disposed between said transduction material and said back matching layer.

7. An acoustic transducer according to claim 1, further comprising a frontal matching structure disposed in front of said transduction material in the desired direction.

8. An acoustic transducer according to claim 7, wherein said frontal matching structure comprises a plurality of frontal matching layers.

9. An acoustic transducer according to claim 8, wherein each of said frontal matching layers is a quarter-wavelength thick based on a selected center frequency.

10. An acoustic transducer according to claim 7, wherein said frontal matching structure is comprised of at least one of epoxy, powder-filled epoxy, porcelain, silicon, silicon glass, quartz glass, polyvinyl chloride, and polyvinylidene fluoride.

11. An acoustic transducer according to claim 1, wherein said transducer is adapted to focus acoustic energy generated by the transducer.

12. An acoustic transducer according to claim 1, wherein said back matching layer is comprised of at least one of epoxy, powder-filled epoxy, porcelain, silicon, silicon glass, quartz glass, polyvinyl chloride, and polyvinylidene fluoride.

13. An acoustic transducer according to claim 1, wherein the magnitude of said transmitted preselected fraction of said sound wave's energy and the magnitude of said reflected preselected fraction of said sound wave's energy vary according to the wavelength of said sound wave.

14. An acoustic transducer according to claim 1, wherein the magnitude of said transmitted preselected fraction of said sound wave's energy and the magnitude of said reflected preselected fraction of said sound wave's energy vary according to an impedance of said back matching layer.

15. An acoustic transducer according to claim 14, wherein said impedance of said back matching layer is at least about 1.5 MRayl and no more than about 10 MRayl.

16. An acoustic transducer according to claim 14, wherein said impedance of said back matching layer is at least about 5 MRayl and no more than about 9 MRayl.

17. An acoustic transducer for transferring acoustic energy between the transducer and a target, comprising:

a plurality of transduction elements, wherein said transduction elements are responsive to electrical energy and generate acoustic energy according to said electrical energy, and are configured to propagate said acoustic energy in at least a desired direction;

an acoustically absorptive backing material disposed behind said transduction material in the desired direction; and a back matching layer disposed between said plurality of transduction elements and said backing material, wherein said back matching layer has an acoustic impedance, and wherein said back matching layer acoustic impedance is selected according to desired at least one of a desired sensitivity parameter, a desired bandwidth parameter, and a desired pulse duration parameter, such that said back matching layer does not completely transmit said acoustic energy and does not completely reflect said acoustic energy.

18. An acoustic transducer according to claim 17, wherein said transducer is adapted to focus acoustic energy generated by the transducer.

19. An acoustic transducer according to claim 17, wherein said transduction material is comprised of at least one of piezoelectric ceramic, piezoelectric crystal, piezoelectric plastic, piezoelectric composite material, lithium niobate, lead zirconate titanate, lead titanate, barium titanate, and lead metaniobate.

20. An acoustic transducer according to claim 17, wherein said transduction elements are substantially acoustically isolated from each other.

21. An acoustic transducer according to claim 20, wherein said transduction elements are separated by an interelement filler comprised of acoustically lossy material.

22. An acoustic transducer according to claim 17, wherein said plurality of transduction elements comprises a 2—2 composite array of transduction elements.

23. An acoustic transducer according to claim 17, further comprising an electrical connection layer disposed between said plurality of transduction elements and said back matching layer.

24. An acoustic transducer according to claim 17, further comprising at least one frontal matching layer disposed in front of said plurality of transduction elements with respect to said desired direction, wherein said frontal matching layer reduces the acoustic impedance between said plurality of transduction elements and the target.

25. An acoustic transducer according to claim 24, wherein said frontal matching layer is comprised of at least one of epoxy, powder-filled epoxy, porcelain, silicon, silicon glass, quartz glass, polyvinyl chloride, and polyvinylidene fluoride.

26. An acoustic transducer according to claim 24, wherein said frontal matching layer comprises a plurality of frontal matching layers.

27. An acoustic transducer according to claim 26, wherein each of said frontal matching layers is a quarter-wavelength thick based on a selected center frequency thick in the desired direction.

28. An acoustic transducer according to claim 17, wherein said impedance of said back matching layer is at least about 5 MRayl and no more than about 9 MRayl.

29. An acoustic transducer according to claim 17, wherein said back matching layer is comprised of at least one of epoxy, powder-filled epoxy, porcelain, silicon, silicon glass, quartz glass, polyvinyl chloride, and polyvinylidene fluoride.

30. An acoustic transducer according to claim 17, wherein the value of said at least one of said desired sensitivity parameter, said desired bandwidth parameter, and said desired pulse duration parameter varies according to the wavelength of the acoustic energy.

31. An acoustic transducer according to claim 17, wherein said impedance of said back matching layer is at least about 1.5 MRayl and no more than about 10 MRayl.

* * * * *